(12) United States Patent
Yeh

(10) Patent No.: US 6,368,309 B1
(45) Date of Patent: Apr. 9, 2002

(54) SMOKE EVACUATION APPARATUS

(75) Inventor: Charles R. Yeh, Plantation, FL (US)

(73) Assignee: Acuderm Inc., Ft. Lauderdale, FL (US)

( * ) Notice: Subject to any disclaimer, the term of this patent is extended or adjusted under 35 U.S.C. 154(b) by 0 days.

(21) Appl. No.: 09/241,808

(22) Filed: Feb. 2, 1999

Related U.S. Application Data

(63) Continuation-in-part of application No. 08/823,869, filed on Mar. 25, 1997, now Pat. No. 5,868,722, which is a continuation of application No. 08/579,615, filed on Dec. 26, 1995, now Pat. No. 5,626,568.

(51) Int. Cl.$^7$ .................................................. A61M 1/00
(52) U.S. Cl. ......................................... 604/315; 604/317
(58) Field of Search ............................ 604/20, 22, 289, 604/310, 312, 313, 315, 317; 454/63, 65, 66

(56) References Cited

U.S. PATENT DOCUMENTS

| | | | |
|---|---|---|---|
| 774,529 A | * | 11/1904 | Nieschange |
| 1,894,905 A | * | 1/1933 | Fechtenburg |
| 2,612,892 A | * | 10/1952 | Beatman |
| 2,927,577 A | * | 3/1960 | Nicolaie |
| 5,380,245 A | * | 1/1995 | Reiterman et al. .......... 604/313 |
| 5,437,651 A | * | 8/1995 | Todd et al. ................. 604/317 |
| 5,626,568 A | * | 5/1997 | Yeh et al. ................... 604/615 |
| 5,769,702 A | * | 6/1998 | Hanson ....................... 454/63 |
| 5,911,222 A | * | 6/1999 | Lawrence et al. .......... 600/573 |
| 6,019,749 A | * | 2/2000 | Fields et al. ................ 604/313 |
| 6,023,639 A | * | 2/2000 | Hakky et al. ................. 604/20 |

* cited by examiner

Primary Examiner—Dennis Ruhl
(74) Attorney, Agent, or Firm—Rockey, Milnamow & Katz, Ltd.

(57) ABSTRACT

This is directed to a smoke evacuator for use in electro surgery and laser surgery to collect smoke and surgical debris which includes body portion, a flared horn portion to promote flow of smoke and surgical debris into the body portion and a filter positioned on the body portion to remove particulate matter contained in the smoke and surgical debris.

6 Claims, 1 Drawing Sheet

SMOKE EVACUATION APPARATUS

CROSS-REFERENCES TO RELATED APPLICATIONS

This application is a continuation-in-part of application Ser. No. 08/823,869, filed Mar. 25, 1997 now U.S. Pat. No. 5,868,722 which, in turn, is a continuation of application Ser. No. 08/579,615 filed Dec. 26, 1995, now U.S. Pat. No. 5,626,568.

BACKGROUND OF THE INVENTION

The present invention is directed to smoke evacuation apparatus, and more particularly to an improved collector for capturing smoke and other airborne debris generated in the course of electrosurgery and laser surgery.

Electrosurgery and laser surgery are found in more widespread use, and particularly in many types of dermatologic, cosmetic and/or plastic surgery procedures. As is well known to those skilled in the art, electrosurgery may involve the use of electrically heated needles which may be used to burn tissue from the surgical site or may involve electrodesiccation and fulguration procedures in which an electric arc is generated between a needle and surgical site.

By the same token, laser surgery is likewise gaining widespread acceptance in procedures in which a laser is used to burn and/or vaporize tissue from a surgical site. Such laser surgical techniques are becoming more widely used in a variety of dermatologic surgery operations. In both electro-surgery and laser procedures, the surgical techniques employed generate a great deal of smoke and other airborne particulate matter in the vicinity of the surgical site. Because such particulate matter itself may be pathogenic, smoke evacuation techniques have been developed to physically remove the smoke and other surgical debris from the surgical site.

A number of smoke evacuators have been developed for that purpose. One particularly successful example is the smoke evacuator described in U.S. Pat. No. 5,423,779 to Charles R. Yeh. While smoke evacuators like that described in the foregoing patent have received widespread acceptance, they may nonetheless operate at less than maximum efficiency in the collection and removal from the surgical site of smoke and surgical debris. One of the reasons that smoke evacuator techniques heretofore used have not been optimally efficient is because the nozzle of the smoke evacuator, in most applications, must be located within approximately two inches of the surgical site.

Otherwise, there is a risk that substantial portions of the smoke and debris thus generated may dissipate into the atmosphere from the surgical site, posing health hazards to health care workers. Indeed, such electrosurgery and laser surgery techniques, because they tend to disperse blood into an aerosol, leave behind such aerosols which can pose a health risk to anyone entering the theater of the surgical operation, even several hours after the surgery has been completed. As will be appreciated by those skilled in the art, such surgical debris, including the blood aerosols above referred to, may contain pathogenic organisms, and particularly viruses. It is important that such debris be collected and removed from the environment as completely as possible.

Substantial improvements in the collection of smoke and debris are described in U.S. Pat. No. 5,626,568. That patent is directed to a smoke evacuator and an improved collector therefor in which a fluid nozzle is positioned adjacent to a surgical site to supply a rapidly moving fluid stream in the area of the surgical site to entrain smoke and surgical debris and therefore effect its removal from the surgical site. Also positioned in the vicinity of the surgical site is a collection nozzle having a flared horn portion positioned to receive the rapidly moving fluid stream having smoke and surgical debris entrained therein. The collection nozzle is connected to an evacuation system to convey the rapidly moving fluid stream having smoke and surgical debris entrained therein.

In the preferred embodiment, the flared horn portion has a hyperbolic configuration to create a flow of fluid in an essentially laminar flow. While the hyperbolic configuration is quite effective in removing smoke and surgical debris from the surgical site, it requires relatively close manufacturing tolerances. In addition, the collector described in the foregoing patent does not include any means for filtering particular matter from the rapidly moving air stream. That function is typically performed by the evacuation system containing appropriate filters for such particulate matter.

It is accordingly an object of the present invention to provide improved apparatus for collecting and removing, with maximum efficiency, smoke and other surgical debris generated as a result of electrosurgical and laser surgical techniques.

It is a more specific object of the present invention to provide apparatus for the collection and removal of smoke and surgical debris in which substantially all of the smoke and surgical debris can be collected and removed from the environment.

It is a more specific object of the invention to provide apparatus for the collection and removal of smoke and surgical debris which can be used to efficiently collect such smoke and debris when used in combination with electrosurgery and laser surgery instruments which can be manufactured inexpensively and which can be provided with a filtration system for collecting particulate matter.

These and other objects and advantages of the invention will appear more fully hereinafter with a description of the present invention.

SUMMARY OF THE INVENTION

The concepts of the present invention reside in a smoke evacuator for use in electrosurgery and laser surgery to collect smoke and surgical debris from a surgical site utilizing a collector having a body portion adapted to be maintained at a reduced pressure. The collector include a flared horn nozzle portion to promote flow of smoke and surgical debris into the body portion for removal from the surgical site. The collector also includes a filter positioned on the body portion to remove particulate matter contained in the smoke and surgical debris from the environment of the surgical site.

In the preferred embodiment, the flared horn nozzle portion is in the nature of a continuous annular lip integral with one end of the body portion. The lip includes a smooth curved surface which extends from the body portion exteriorly therefrom so that the lip includes a surface portion having a hemispherical cross-section so that the lip extends downwardly in a direction substantially parallel to the interior walls of the body portion. It has been found that the use of such a lip promotes a smooth laminar flow of a fluid stream containing smoke and surgical debris entrained therein from the environment of the surgical site into the body portion of the collector for removal of the smoke and surgical debris from the environment of the surgical site. Such lip configuration also serves to expand the field of influence thereby assuring the complete capture of smoke and debris.

Thus, in use, the collector can be connected to a source of reduced pressure to maintain the body portion at a reduced pressure whereby a fluid stream from the surgical site is drawn around the lip and into the body portion of the collector whereby smoke and surgical debris entrained in the fluid stream is removed from the surgical site. As the entrained smoke and surgical debris is drawn into the body portion of the of the collector, the filter positioned thereon serves to remove particulate matter and blood aerosols from the environment of the surgical site. It has been found that the collector of the present invention is simple and inexpensive to manufacture and use. In addition, it can be fabricated out of inexpensive materials and thus is disposable after use to avoid biohazard and contamination of subsequent surgical operations.

DETAILED DESCRIPTION OF THE INVENTION

Figure 1:
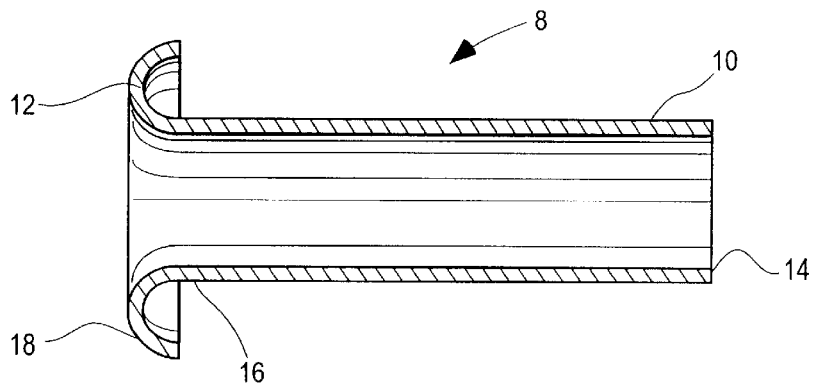
FIG. 1 is a cross-sectional view of a collector embodying the concepts of the present invention.

Referring now to FIG. 1 is a detailed description of the smoke evacuator of the present invention, there is illustrated in that figure a collector 8 embodying the features of the present invention having generally cylindrical walls 10 and a flared horn nozzle portion 12, preferably integral therewith. The body portion of the collector of the present invention includes a distal end 14 adapted to be connected to a source of reduced pressure. As will be appreciated by those skilled in the art, the source of reduced pressure may be a vacuum pump or an exhaust fan to reduce the pressure within the body portion 10. Alternatively, the source of reduced pressure may also be a smoke evacuator of the type described in U.S. Pat. No. 5,243,779.

In accordance with the practice of the invention, the distal portion 16 of the body portion 10 includes a generally hemispherical lip 18 integral with the side walls of the body portion 10 defining a smooth arcuate surface extending from the proximal end 16 of the body portion 10 substantially 180 degrees. It has been found, as noted above, that the use of such a hemispherical lip as part of the flared horn portion 12 serves to promote laminar flow of a fluid, and preferably room air, into the body portion 10 of the collector when the body portion is maintained at a reduced pressure. In that way, smoke and surgical debris in the environment of the surgical site becomes, by reason of the increased field of influence, entrained in the fluid stream and is drawn into the collector for removal from the environment of the surgical site.

Figure 2:
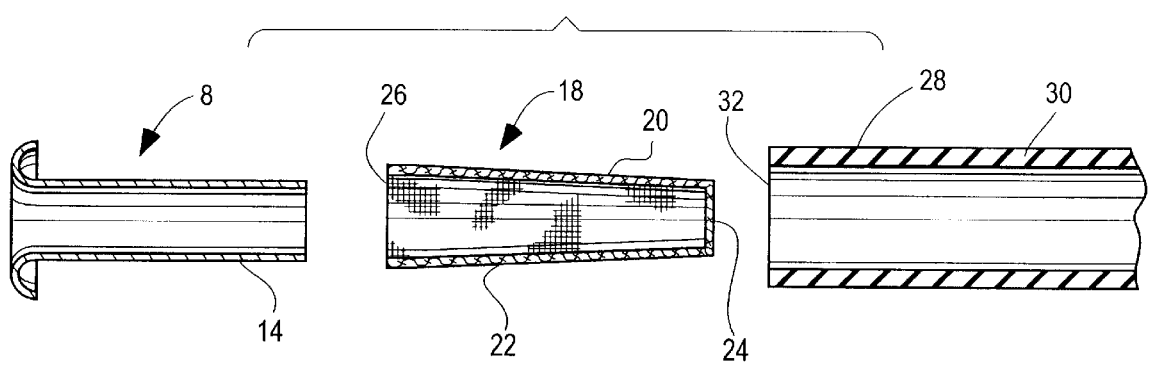
FIG. 2 is an exploded view illustrating the collector, the filter and associated plumbing of the smoke evacuator of the present invention.

As shown in FIG. 2, the collector 8 is part of an assembly of elements for removal of smoke and surgical debris from the surgical site. Positioned for attachment on the proximal end 14 of the collector 8 is a filter 18, preferably in the form of a sock-type filter having side walls 20 and 22, respectively and a bottom wall 24. The filter 18 can be made of a wide variety of materials suitable for use in the filtration of particulate matter from fluid streams. For example, the filter 18 can be fabricated from loosely woven or non-woven natural or synthetic fibers whereby the interstices between the fibers are sufficiently small to permit the passage of a fluid such as air therethrough but do not permit passage of large smoke particles and other particulate matter generated as a result of electrosurgical or laser surgical operations. In addition, the filter 18 also serves to prevent the ingestion of surgical equipment present in the environment of the surgical site, including such equipment as surgical sponges and the like. For example, in the preferred practice of the invention, the interstices between the fibers making up the filter 18 should be sufficiently small so as to entrap, for example, droplets of blood or other bodily fluid which may contain infectious agents.

The filter includes a mouth portion 26 dimensioned to correspond to the proximal end portion 14 of the collector 8 in a tight fitting relationship. In that way, the mouth 26 of the filter 18 can be removably attached to the proximal portion of the collector 8 to secure the filter element thereon.

Figure 3:
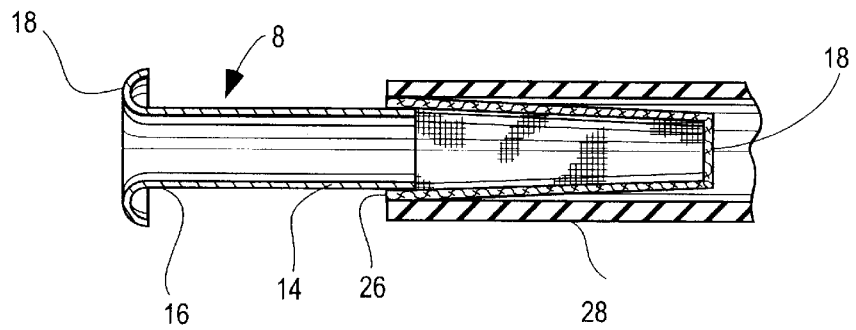
FIG. 3 is a cross-sectional view illustrating the assembly of the collector of the present invention with a filter mounted and adapted to be connected to a source of reduced pressure.

Also making up the assembly of the smoke evacuator of the present invention is a conduit 28 connected to a source of reduced pressure. The conduit 28 is preferably formed of a cylindrical wall 30 having a distal opening 32 at one end thereof. The opening 32 is dimensioned to correspond to the dimension of the filter element 18 positioned on the distal portion 14 of the horn 8. In its simplest form, the conduit 28 can simply be an elastomeric hose adapted to be tightly fit over the filter element 18 once it has been positioned on the proximal end 14 of the collector 8. The assembly of the components is shown in FIG. 3 of the drawings including the collector 8 having its hemispherical lip 18 on the distal end 16 thereof. Mounted on the proximal end 14 of the collector 8 is the mouth 26 of the filter 18. The filter 18 is thus sandwiched between the proximal end portion 14 of the collector 18 and the conduit 28 whereby the conduit 28 and the filter are each securely but removable attached to the proximal portion 14 of the collector 8. If desired, various conventional clamping equipment may be used to secure the sandwiching of the filter between the conduit 28 and the proximal end portion 14 of the collector 8. Since the nature of such clamping means forms no part of the invention, it is not illustrated in the drawings for purposes of simplicity.

In use, the flared horn portion 12 of the collector 8 is positioned adjacent a surgical site and is connected by means of the conduit 28 to a source of reduced pressure. That source of reduced pressure reduces the pressure within the body portion 10 of the collector 8, causing room air to be drawn over the hemispherical surface 18 of the flared horn portion 12 into the interior of the collector 8. As a result, smoke and surgical debris generated during electrosurgical operations or laser surgical operations becomes entrained in the room air and drawn into the collector 8. Because the collector is attached to a source of reduced pressure by means of a conduit 28, the smoke and surgical debris is caused to pass through the filter 18 from which particulate matter is removed and maintained within the confines of the filter 18. That represents a substantial advantage in that particulate matter including particles of smoke, tissue fragments and/or droplets of bodily fluids which might otherwise contain harmful pathogens are trapped within the filter 18 and thus removed from the environment of the surgical site. That, in turn, permits filters on the smoke evacuator to which the nozzle is connected to function more efficiently.

It will be understood that various changes and modifications can be made in the details of configuration and use without departing from the spirit of the invention as will be especially defined in the following claims.

What is claimed is:

1. A smoke evacuator for use in electrosurgery and laser surgery to collect smoke and surgical debris from a surgical site comprising:
   (a) a body portion adapted to be maintained at a reduced pressure;
   (b) a flared horn nozzle portion to promote flow of smoke and surgical debris into the body portion for removal from the surgical site; and
   (c) a filter positioned on the body portion to remove particulate matter contained in the smoke and surgical debris, said filter formed of a woven or non-woven fabric having interstices therebetween wherein the interstices are sufficiently small to block passage of particulate matter therethrough.

2. A smoke evacuator as defined in claim 1 wherein the flared horn nozzle portion is in the form of an annular lip.

3. A smoke evacuator as defined in claim 2 wherein the lip defines a hemispherical surface extending downwardly in a direction substantially parallel to the interior surface of the body portion.

4. A smoke evacuator as defined in claim 1 wherein the body portion has a proximal portion and the filter is mounted on the proximal portion.

5. A smoke evacuator as defined in claim 1 which includes a conduit adapted to be connected to a source of reduced pressure overlaying the filter whereby particulate matter is drawn into the body portion passing into the filter to filter particulate matter.

6. A smoke evacuator as defined in claim 1 wherein the filter is formed of a woven or non-woven fabric being made from fabric having interstices therebetween wherein the interstices are sufficiently small to block passage of particulate matter therethrough.

\* \* \* \* \*